United States Patent
Benditte-Klepetko (10) Patent No.: US 11,341,619 B2
(45) Date of Patent: *May 24, 2022

(54) METHOD TO PROVIDE A VIDEO WITH A COMPUTER-MODIFIED VISUAL OF A DESIRED FACE OF A PERSON

(71) Applicant: QuantiFace GmbH, Vienna (AT)

(72) Inventor: Heike Benditte-Klepetko, Vienna (AT)

(73) Assignee: QuantiFace GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 17/331,195

(22) Filed: May 26, 2021

(65) Prior Publication Data
US 2021/0279844 A1    Sep. 9, 2021

Related U.S. Application Data

(63) Continuation of application No. 17/117,748, filed on Dec. 10, 2020.

(30) Foreign Application Priority Data

Dec. 11, 2019   (EP) ..................................... 19215139

(51) Int. Cl.
*G06T 7/194*    (2017.01)
*G06T 7/11*     (2017.01)
(Continued)

(52) U.S. Cl.
CPC ............ *G06T 5/005* (2013.01); *G06T 7/0002* (2013.01); *G06T 7/11* (2017.01); *G06T 7/194* (2017.01);
(Continued)

(58) Field of Classification Search
CPC . G06T 5/005; G06T 7/194; G06T 7/11; G06T 7/0002; G06T 2200/24;
(Continued)

(56) References Cited

U.S. PATENT DOCUMENTS

| 9,875,391 B2 | 1/2018 | Liang et al. |
| 10,289,897 B2 | 5/2019 | Tang et al. |

(Continued)

FOREIGN PATENT DOCUMENTS

| WO | 2015/017687 A2 | 2/2015 |
| WO | 2017177259 | 10/2017 |

OTHER PUBLICATIONS

Klepetko, H., "Facial Characteristics and First Impression: wie der 'Erste Eindruck' die Wahl der Therapie beeninflussen kann," Schein & Sein, Austria, Sep. 12-14, 2019.

(Continued)

*Primary Examiner* — Thai Q Tran
*Assistant Examiner* — Jose M Mesa
(74) *Attorney, Agent, or Firm* — Merchant & Gould P.C.

(57) ABSTRACT

At least one characteristic of a face of the person to be improved is inputted. Artificial intelligence is used to analyse a visual of the person's face and generate data sets of modifications to improve the visual appearance of the person in different ways towards a selected characteristic. The visual of the face of the person is modified based on the data sets of modifications and computer-modified visuals of the face of the person are generated and displayed. One of the computer-modified visuals is selected as the desired face of the person. A video is provided that shows a computer-modified visual of the desired face of the person.

12 Claims, 4 Drawing Sheets

(51) Int. Cl.
    *G11B 27/036*     (2006.01)
    *H04N 7/15*     (2006.01)
    *G06T 5/00*     (2006.01)
    *G06T 7/00*     (2017.01)
    *G06V 40/16*     (2022.01)

(52) U.S. Cl.
    CPC .......... *G06V 40/161* (2022.01); *G06V 40/174* (2022.01); *G11B 27/036* (2013.01); *H04N 7/15* (2013.01); *G06T 2200/24* (2013.01); *G06T 2207/10016* (2013.01); *G06T 2207/20081* (2013.01); *G06T 2207/30201* (2013.01)

(58) Field of Classification Search
    CPC . G06T 2207/10016; G06T 2207/20081; G06T 2207/30201; G06K 9/00228; G06K 9/00302; G11B 27/036; H04N 7/15
    See application file for complete search history.

(56) References Cited

U.S. PATENT DOCUMENTS

| | | | |
|---|---|---|---|
| 10,387,714 B2 | 8/2019 | Han et al. | |
| 10,446,189 B2 | 10/2019 | Zukerman | |
| 10,482,333 B1 * | 11/2019 | el Kaliouby | B60R 11/04 |
| 10,764,535 B1 * | 9/2020 | Powell | H04N 7/147 |
| 10,796,480 B2 * | 10/2020 | Chen | G06T 7/50 |
| 10,825,564 B1 | 11/2020 | Zhang | |
| 10,997,703 B1 | 5/2021 | Khalatian | |
| 11,151,362 B2 | 10/2021 | Velthuis et al. | |
| 2006/0204106 A1 | 9/2006 | Yamaguchi | |
| 2010/0202696 A1 | 8/2010 | Usui | |
| 2012/0257800 A1 | 10/2012 | Zheng | |
| 2013/0069940 A1 | 3/2013 | Sun et al. | |
| 2014/0112534 A1 | 4/2014 | Sako | |
| 2015/0279113 A1 | 10/2015 | Knorr | |
| 2016/0307027 A1 | 10/2016 | Liang et al. | |
| 2018/0293802 A1 | 10/2018 | Hendricks et al. | |
| 2018/0315063 A1 | 11/2018 | Cheesman | |
| 2018/0342110 A1 | 11/2018 | Miao | |
| 2019/0005306 A1 | 1/2019 | Wu | |
| 2019/0005359 A1 | 1/2019 | Wilf et al. | |
| 2020/0320791 A1 | 10/2020 | Yeh | |
| 2020/0357174 A1 | 11/2020 | Banerjee | |
| 2021/0012097 A1 | 1/2021 | Velthuis et al. | |
| 2021/0089759 A1 | 3/2021 | Todorov et al. | |
| 2021/0183021 A1 | 6/2021 | Benditte-Klepetko | |
| 2021/0183124 A1 | 6/2021 | Benditte-Klepetko | |
| 2021/0279933 A1 | 9/2021 | Benditte-Klepetko | |

OTHER PUBLICATIONS

Klepetko, H., "Facial Characteristics: Letting Social Judgment Determine our Choice of Treatment," International Society of Plastic Surgery (ISAPS), 2018.
Qin, R. et al., "Modern Physiognomy: An Investigation on Predicting Personality Traits and Intelligence from Human Face", Arxiv.org, Cornell University Library, Ithaca, NY Apr. 26, 2016.
Kamenskaya, E., et al., "Recognition of Psychological Characteristics from Face", Metody Informatyki Stosowanej, Gdansk Poland, http://www.uniphiz.com/digital_physiognomy/recognition-of-pyschological-characteristics-from-face.pdf (2008).
Jacques, Jr., J.C.S., et al., "First Impressions: A Survey on Vision-Based Apparent Personality Trait Analysis", Arxiv.org, Cornell University Library, Ithaca, NY Apr. 22, 2018.
Messer, U., et al., "Predicting Social Perception from Faces—A Deep Learning Approach", Arxiv.org, Cornell University Library, Ithaca, NY, (Jun. 29, 2019).
Liao, Y., et al., "Deep Rank Learning for Facial Attractiveness", 2017 4th IAPR Asian Conference on Pattern Recognition (ACPR), IEEE, (Nov. 26, 2017).
European Search Report, Application No. EP 19 21 5134, dated Jul. 17, 2020.
European Search Report, Application No. EP 19 21 5139, dated Jun. 16, 2020.
Gunes, H. et al., "Comparative beauty classification for pre-surgery planning", Systems, Man and Cybernetics, 2004, IEEE, vol. 3, Oct. 10, 2004, pp. 2168-2174.
Manavis, Sarah, "How Instagram's plastic surgery filters are warping the way we see our faces", NewStatesman, Oct. 29, 2019, retreived on Feb. 10, 2021 from internet: https://newstatesman.com/science-tech/social-media/2019/10/how-instagram-plastic-surgery-filter-ban-are-destroying-how-we-see-our-faces, 5 pages.
Park, Jungsik, et al., "A Framework for Real-Time 3D Freeform Manipulation of Facial Video", Applied Sciences, vol. 9, No. 21, Nov. 4, 2019, p. 4707, pp. 1-10.
PCT International Search Report and Written Opinion in International Application PCT/EP2020/083540, dated Feb. 24, 2021, 12 pages.
PCT International Search Report and Written Opinion in International Application PCT/EP2020/083543, dated Feb. 11, 2021, 11 pages.

* cited by examiner

| Dominant Face Area | zygoma | lower eyelid | lips | chin | cheek | jawline | eyebrows | marionett line | glabella |
|---|---|---|---|---|---|---|---|---|---|
| Action | more volume | | | | more volume | more volume | lower | | |
| Treatment | fillers facelift | | | | fillers facelift | fillers | botox | | |
| Competent Face Area | zygoma | lower eyelid | lips | chin | cheek | jawline | eyebrows | marionett line | glabella |
| Action | | | | less wide | less full | | lower | | |
| Treatment | | | | bone correction facelift filler | fat resection lipolysis filler | | botox | | |
| Trustworthy Face Area | zygoma | lower eyelid | lips | chin | cheek | jawline | eyebrows | marionett line | glabella |
| Action | | | higher lateral | less wide | pronounced cheekbones | | higher medial | | |
| Treatment | | | fillers botox surgical correction | bone correction facelift filler | fillers | | botox | | |
| Younger Face Area | zygoma | lower eyelid | lips | chin | cheek | jawline | eyebrows | marionett line | glabella |
| Action | more volume | smooth | fuller | | | straight | lateral | smooth | smooth |
| Treatment | fillers facelift | blepharoplasty fillers | fillers surgical correction botox | | | facelift fillers | botox fillers threats eyebrow lift surgical | fillers botox threats facelift | botox fillers threats |

Fig. 5

COMPETENT

METHOD TO PROVIDE A VIDEO WITH A COMPUTER-MODIFIED VISUAL OF A DESIRED FACE OF A PERSON

CROSS REFERENCE TO RELATED APPLICATION

This application is a continuation of U.S. application Ser. No. 17/117,748 filed Dec. 10, 2020, which claims benefit of European Patent Application Serial No. 19215139.7, filed Dec. 11, 2019, and which applications are incorporated herein by reference in their entirety. To the extent appropriate, a claim of priority is made to the above disclosed applications.

BACKGROUND

The present invention relates to a method and device to provide a video with a computer-modified visual of a desired face of a person. There is a general wish to improve the own appearance in personal interactions in a private or business environment. The face is one of the main areas of the body relevant for this appearance. The appearance is then categorized by others in the course of forming a first impression in a complex way. Characteristics attributed to a person when making a first impression are, for example, attractiveness, healthiness, youthfulness, tiredness, sadness, friendliness, dominance, competence, likability or trustworthiness just to name some of these. A person may want to improve his/her first impression as being perceived as dominant or competent in a video conference with customers, but may want to improve his/her first impression as being perceived as likeable and trustworthy in an evening video call with his/her family when being on a business trip. Another person using a partnership online platform may want to improve his/her first impression as being perceived as attractive or sexy by potential partners.

WO 2015/017687A2 discloses a method and system with a server that determines the level of "severity" of a defect in a selected anatomical area. The server for instance analyses a photo of a person to rate wrinkles at the eyes in line with a standardized wrinkle rating. The server uses a database with the likely outcome of a selected medical or cosmetic treatment for the selected anatomical area to support a person in her/his decision about a medical or cosmetic treatment.

US 2019/0005359 A1 discloses a method and system that processes a computer program to train an artificial intelligence that provides an automated rating of the characteristic of a visual of a face of a person. To achieve that a data set of visuals of faces and extracted face property data thereof linked to face characteristics data provided by a representative set of humans that rate the visuals of these faces about their face characteristics are generated and stored in a database. Face property data of further visuals of faces are extracted and used together with the generated data set in the database for training of the artificial intelligence to enable the artificial intelligence to provide an automated rating of the characteristics of the visuals of faces. US 2019/0005359 A1 furthermore discloses to use the artificial intelligence to rate photos of different persons about their first impression for the characteristic "dominance" to support an HR manager in his decision which candidate to choose for a new job. In another embodiment a face-based personality analyse is processed based on a video that shows one or more persons like in a video conference.

SUMMARY

None of these prior art methods and systems provide technical means to support a person in his/her general wish to improve the own first impression as seen and categorized by other persons. These problems are solved with a method that comprises the following steps:

Provide at least one visual of the face of the person;
Input at least one characteristic of the face of the person to be improved;
Use the artificial intelligence to analyse the visual of the person's face and to generate at least two data sets of modifications to improve the visual appearance of the person in at least two different ways towards the selected characteristic;
Modify the visual of the face of the person based on both data sets of modifications and generate two computer-modified visuals of the face of the person;
Display both computer-modified visuals of the face of the person;
Select one of the two computer-modified visuals as the desired face of the person;
Provide a video that shows the face of the person and use the selected data set of modifications of the selected desired face of the person to modify the video to provide the video with the computer-modified visual of the desired face of the person.

The invention is based on the finding that when aiming to understand a person's appearance it is only a secondary goal to e.g. look how much wrinkles a person has since persons categorize the appearance of others in the course of forming a first impression in a more complex way and as a whole. Characteristics attributed to a person when making a first impression are, for example, attractiveness, healthiness, youthfulness, tiredness, sadness, friendliness, dominance, competence, likability or trustworthiness just to name some of these.

This inventive method, device and/or computer program uses a completely new concept and technique to enable a person to improve his/her first impression in a live video conference or stored video message as selected by the person. An improvement in a characteristic attributed by others during forming the first impression can be achieved in both ways, i.e. increasing a characteristic which is perceived as positive or decreasing a characteristic which is perceived as negative. The person selects what characteristic to improve for the upcoming video conference and sends a visual (photo or video) of his/her face to see what kind of different improvements for this characteristic are possible. Based on the classification of the artificial intelligence about the characteristics of the person in his/her photo or video the artificial intelligence proposes at least two sets of modifications how to modify the visual to improve the selected characteristic based on information stored in the database. To e.g. improve the characteristic "competence" the eyebrow position needs to be lifted and the volume of the jawline needs to be increased. This first set of modifications of the face of the person would in principle be possible in real life by a cosmetic and/or medical treatment of the person. Based on the inventive concept there is no limit to only provide sets of modifications and display only improvements that are within the borders of cosmetic and/or medical treatments. Therefore, the second set of modifications could for instance include modifications that reduce or increase the distance of the eyes or the distance between the eyes and the mouth or drastically change the form or size of the eyes, mouth or ears. Further sets of modifications may include objects a person may wear like glasses or earrings to change his/her first impression for other persons. All these different kind of sets of modifications of the visual of the face provided by the person are generated and provided by the artificial intelligence that in a next step modifies the visual and displays all possible computer-modified visuals of the face of the person. The person selects the one visual with the improved selected characteristic and choses his or her desired face for the upcoming video conference. In a final step of the inventive method the artificial intelligence identifies the face of the person in the live video and replaces it continuously with the desired face of the person. This provides the major advantage, that the person may select for each video conference or even during a video conference how he/she would like to support his/her message with the appropriate visual appearance. A person is of course fee to select one or more characteristics to improve his/her visual appearance.

In a preferred embodiment the artificial intelligence analyses the content and tone of a conversation in a video conference and in case the person changes from a silent and truthful behaviour into a loud shouting and aggressive behaviour, the artificial intelligence at the same time changes the visual appearance of the face to support his/her actual message. These changes of the visual appearance may be in small steps and subtle, to be only recognized subconsciously by the other participants of the conference, or dramatic, as selected by the person.

BRIEF DESCRIPTION OF THE DRAWINGS

These and further advantageous embodiments of the invention will be explained based on the following description and the accompanying drawings.

DETAILED DESCRIPTION

Figure 1:
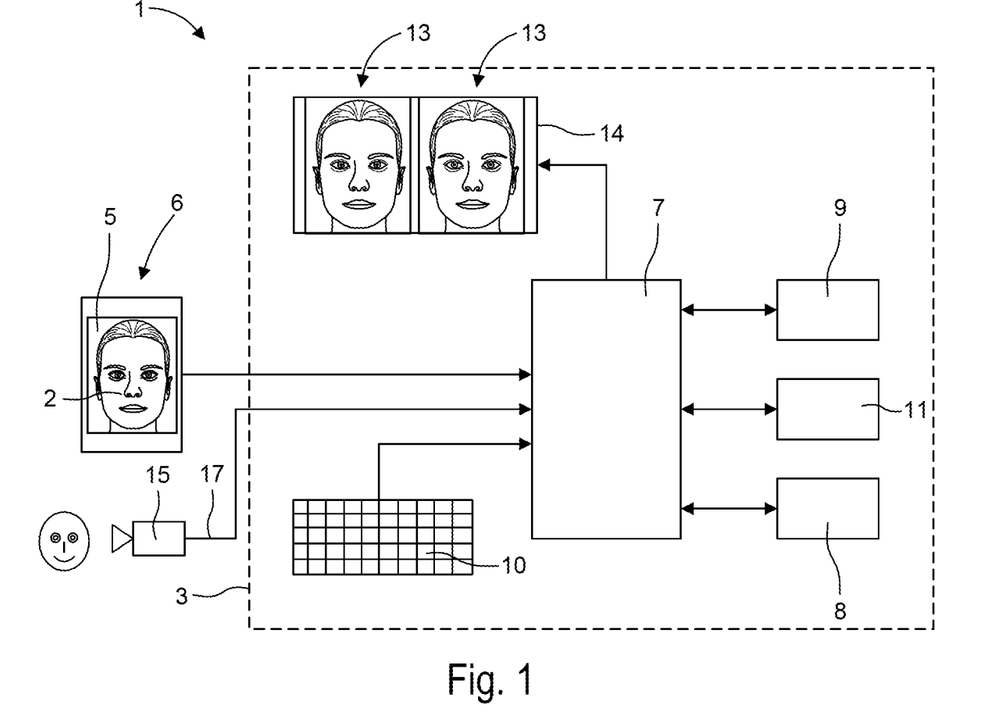
FIG. 1 shows a system to provide a video with a computer-modified visual of a desired face of a person.
Figure 2:
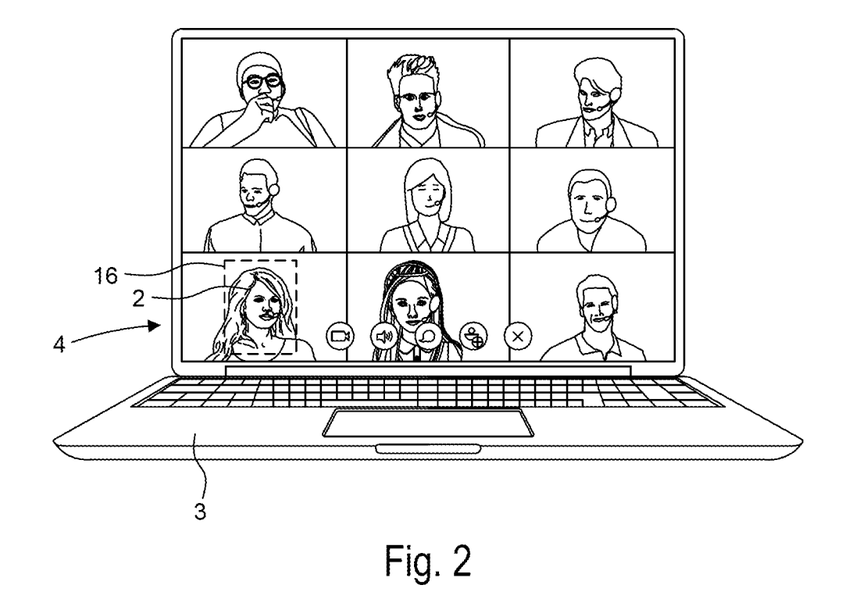
FIG. 2 shows a device of the system with an ongoing video conference and the computer-modified face of the person.

FIG. 1 shows a system 1 to display a video with a computer-modified visual of a desired face of a person 2 with a device 3. The device 3 could be a mobile device or a computer to processes a software and in particular an App for person 2, who wants to modify her visual first impression as seen by other persons. As an example person 2 wants to join a live video conference 4 with device 3 as shown in FIG. 2, but she would like improve her characteristic "competence" to look more competent than she does in real life to increase her chances to be successful in this video conference 4. To achieve that she only needs to select one photo 5 or a video that shows her normal face and in this example sends this photo 5 from her mobile phone 6 to device 3 for further processing.

Device 3 processes a deep learning based application 7 or artificial intelligence that analyses visual data representing photo 5 or a video of the face of person 2 to rate one or more characteristics attributed to person 2 when making a first impression. Such face characteristics may for example be attractiveness, healthiness, youthfulness, tiredness, sadness, friendliness, dominance, competence, likability or trustworthiness. The deep learning based application 7 is a computer program comprising instructions which, when the program is executed by device 3, causes device 3 to carry out the following steps to display a video with a computer-modified visual of the desired face of person 2.

In a first step of the method, a data set of visual data of visuals of faces and extracted face property data thereof linked to face characteristics data is generated. To extract face properties conventional computer vision algorithms like a landmark detection divide the face of persons in regions like the chin and the jawline and automatically extract characteristics and their location in the face. Such face property data may for instance include the distance between the eyes or the distance between the eyes and the mouth and other distances to be measure to describe a face. These face property data are stored together with the visual data (photo or video) of these faces by the deep learning based application 7 in a database 8 of the device 3. A representative number of such visuals of faces stored as visual data in database 8 are shown on a display to a representative number of humans to manually rate these visuals of faces about their characteristics. The humans may rate them with scores (e.g. from 0 to 7) for different characteristics. These human ratings are stored in database 8 linked to the visual data of the faces and provide a basis information for the deep learning based application 7 to automatically rate characteristics attributed to a person 2 when making a first impression.

Figure 3:
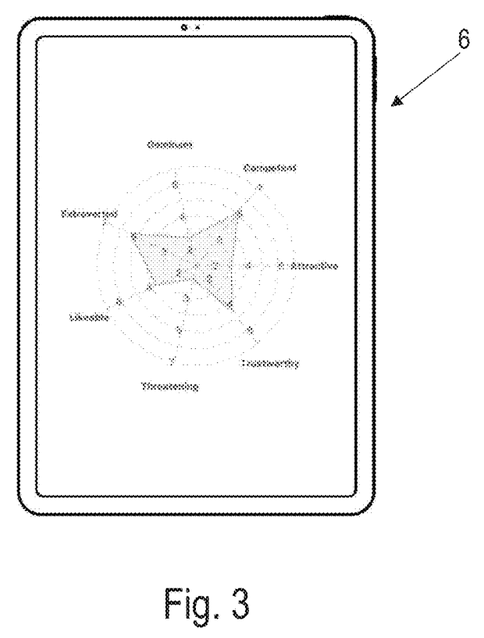
FIG. 3 shows a description and rating of the characteristics based on the visual data of the person's face.

In a second step face property data of these visuals of faces are extracted by the conventional computer vision algorithms for example landmark detection, wrinkle detection, skin texture analysis or analysis of facial proportions. These face property data of visuals of faces are used together with the data set generated and stored in database 8 in the first step for training of the deep learning based application 7 to enable the artificial intelligence to provide an improved automated rating of the characteristics of the visuals of faces. As a result, any visual of a face may be provided to the deep learning based application 7, which will be based on the data set stored in database 8 provide an automated rating of the characteristics of the visuals of the face. FIG. 3 shows such a description and result of the automated rating of the characteristics of a person based on the visuals of the person's face displayed on mobile phone 6. Such kind of an artificial intelligence for automated rating of the characteristics of a person based on visuals of the person is known to a man skilled in the art from US 2019/0005359 A1 and therefore not discussed in more detail here.

After database 8 has been setup with above described steps, system 1 is ready to be used to display a video with a computer-modified visual of a desired face of a person 2 with a device 3 as described in the following steps of the method.

In a third step at least one visual (photo or video) of person 2 has to be provided to device 3. As in this example person 2 selects the one photo 5 that shows her normal face and sends this photo 5 from her mobile phone 6 to device 3 for further processing. In principle, photos may be taken in a standardized or a non-standardized way. Instructions for a person and/or a photographer to take a standardized photo may include one or more of the following steps: ask the person to take off e.g. earrings or a nose ring; ask the person not to smile, ask the person to make a neutral facial expression; ask the person to keep head hair out of his/her face; ask the person to look straight into the camera; good general condition of lightning; neutral background. Photo 5 shown in FIG. 1 as an example has been taken as a standardized photo. If photo 5 had been taken in a non-standardized way, the automated rating by deep learning based application 7 would be more difficult, but possible as well. Therefore, device 3 comprises visual data modification means 9 to pre-process the provided photo 5 or video of the face of person 2 in an attempt to standardize their content prior to the analysis of deep learning based application 7 as much as possible. The pre-processing of photo 5 may include one or more of the following steps: cut-out the background behind the face from the visual data; cut-out the ears of the person's face to reduce the visual influence of e.g. earrings; cut-out clothes and other wardrobe that might influence with the face; cut-out the head hair of the person 2. Of course if person 2 on photo 5 does look to one side, then it will not be possible to pre-process this photo 5 into a standardized photo 5 like the one shown in FIG. 1. The visual data of photo 5 are sent from mobile phone 6 to device 3.

Figure 4:
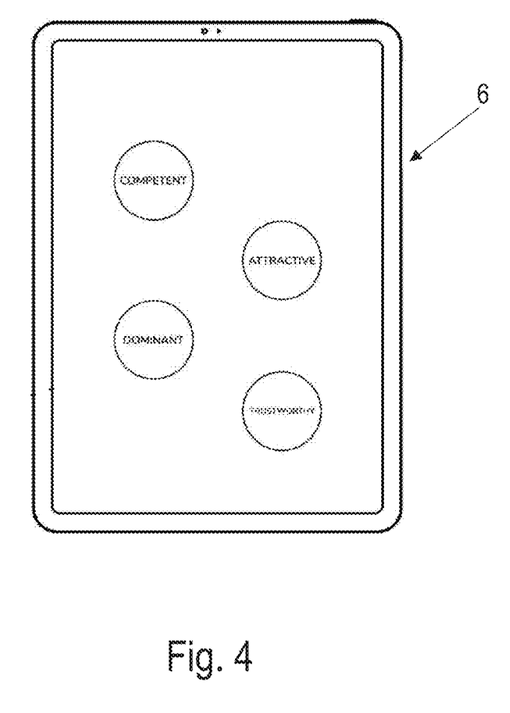
FIG. 4 shows how characteristics may be selected by the user in an App.

In a fourth step person 2 uses input means 10 to input at least one characteristic of her face she would like to improve, which selected characteristic is transferred as face characteristics data to deep learning based application 7 of device 3. In another embodiment, person 2 uses input means of the App of mobile phone 6 as shown in FIG. 4 where a button is realized for each characteristic a person may select. According to above explained example person 2 selects "competent" as characteristic, which is transmitted via broadband network to deep learning based application 7 of device 3. In another embodiment of the invention person 2 may use another way to input the at least one characteristic with mobile phone 6. This may be done by the selection of the App used by person 2, as there may be an App to select the characteristic "attractive" and another App to select the characteristic "competent".

In a fifth step of the method the deep learning based application 7 of device 3 analyses visual data of photo 5 of person 2. As a result, learning based application 7 rates the characteristics of person 2 based on photo 5 and in particular evaluates and rates the characteristic "competent" of person 2.

To achieve that technical step, the deep learning based application 7, based on database 8, extracts face properties of photo 5 by dividing the face of person 2 in photo 5 in regions like the chin and the jawline. If photo 5 sent from mobile phone 6 is a non-standardized photo 5, then deep learning based application 7 is used to fill missing visual information or to estimate how the face on this photo 5 would look like if taken in a standardized way to enable a more or less standardized rating of the characteristics. As a result of this analysis device 3 scores 5 points for the characteristic "competent" with a scale from 0 to 7 points as can be seen in FIG. 3.

Figure 5:
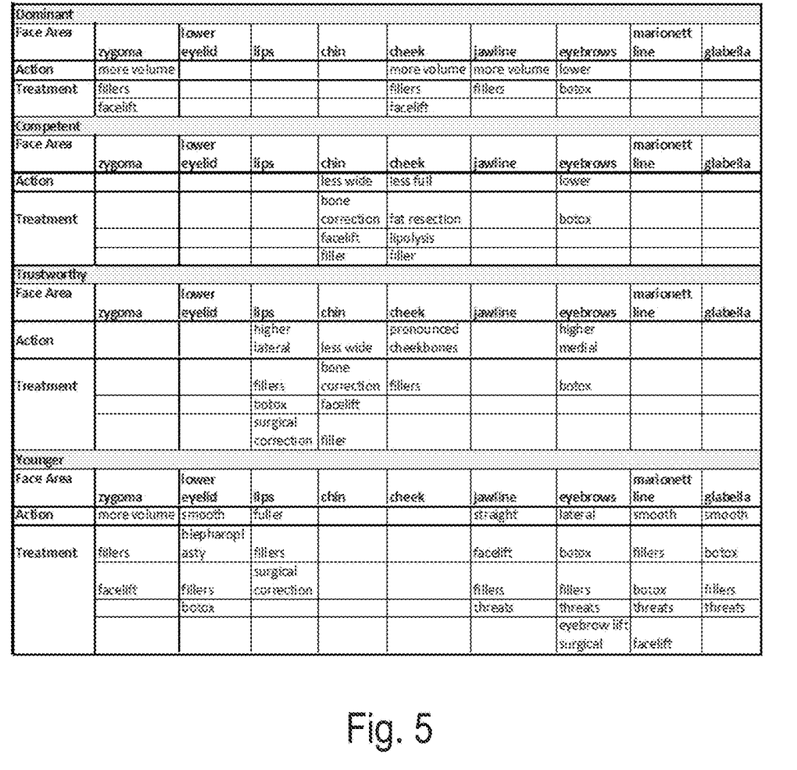
FIG. 5 shows a table with examples of invasive and/or minimally invasive cosmetic and medical treatments to achieve changes of a desired characteristic of a person's face.
Figure 6:
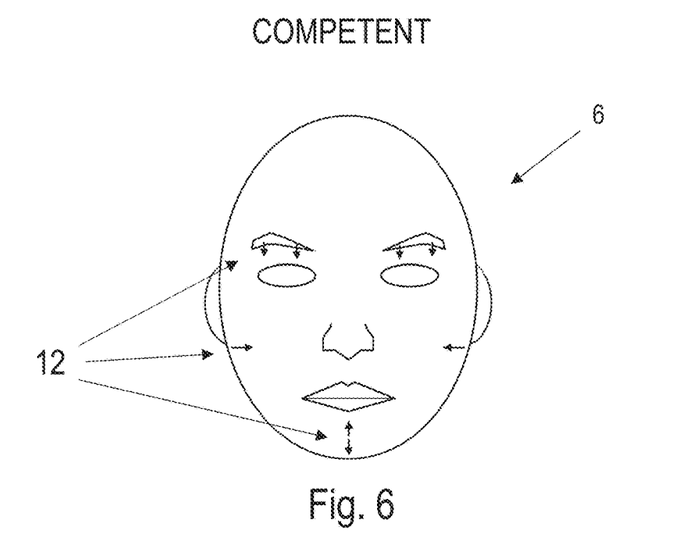
FIG. 6 shows a line drawing of the face of a person with a data set of modifications how to improve the characteristic "competent".

FIG. 5 shows a table with examples of invasive and/or minimally invasive cosmetic and medical treatments to achieve changes of a desired characteristic of a person's face, which table is based on clinical studies. Such data are stored in a modification data base 11 of device 3. With some or a combination of these treatments the desired characteristic may be improved by 1 or more points in the rating when processing a real treatment of a real person. But the inventive concept is not limited by achievements of real treatments and furthermore stores data in modification data base 11 that provide an improvement of a characteristic, but in a way a real person would not be treated. So in one example the distance between the eyes would need to be increased significantly to improve one characteristic, which would not be an option in real life. Deep learning based application 7 based on data stored in modification data base 11 is built to provide not only one, but several data sets of modifications 12 which indicate areas in the face of the visual of person 2 which need to be modified by visual data modification means 9 to improve the desired selected characteristic in different ways and with different scores of improvement. FIG. 6 shows a line drawing of the face of person 2 with a first data set of modifications 12 how to improve the characteristic "competent" based on invasive and/or minimally invasive cosmetic and medical treatments listed in FIG. 5. Deep learning based application 7 based on further data in modification data base 11 provides a second data set of modifications 12 how to improve the characteristic "competent" based on modifications that would not be possible with real persons, but provide a very good improvement of the desired selected characteristic and still look realistic in a way that person 2 still is recognized as the person 2 she is. In this way, deep learning based application 7 may provide several sets of modifications 12, some with subtle improvements, which will be only recognized subconsciously, and others with recognizable improvements and some with dramatic improvements of the score of the selected characteristic.

Figure 7:
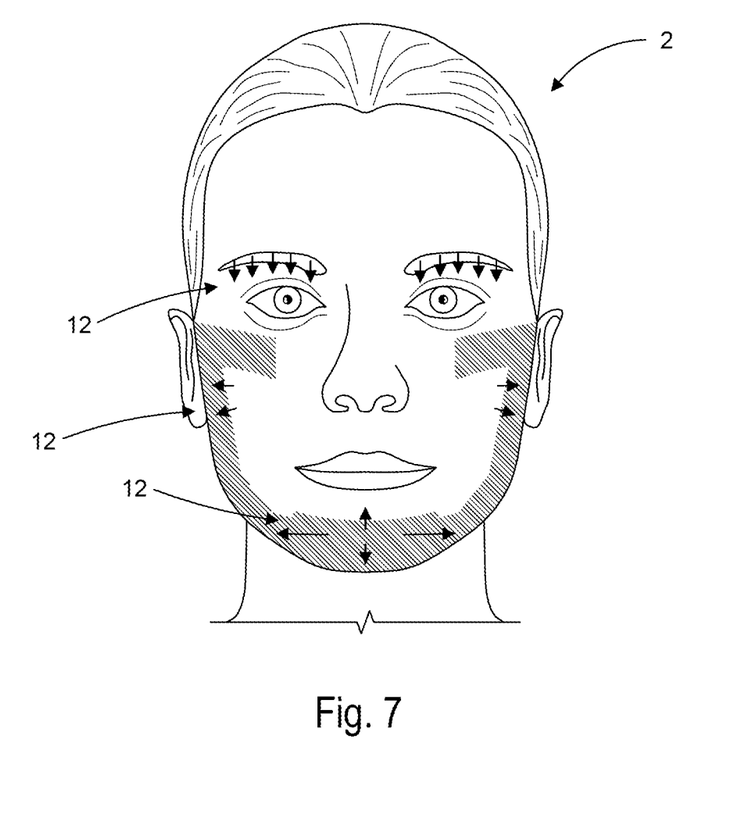
FIG. 7 shows a photo of a face of a person with regions of the face marked to be treated to increase the characteristic "dominant" attributed to the person when making a first impression.

In a sixth step of the method visual data modification means 9 modify the photo 5 of person 2 with each of the two or more data sets of modifications 12 and generate two or more computer-modified photos 13 of the face of person 2. Data sets of modifications 12 technically are code instructions that are needed to modify the photo like in a software program PhotoShop®. FIG. 7 as another example shows the face of person 2 with another data set of modifications 12 how to improve the characteristic "dominant" based on invasive and/or minimally invasive cosmetic and medical treatments.

In a seventh step of the method a display 14 of device 3 is used to show person 2 all computer-modified photos 13 to enable her to select her desired modified facial appearance in the video conference 4 to come. She therefore may select between stronger improvements of the selected characteristic "competent" and less strong improvements of this characteristic and in an eighth step of the method decides which of the displayed computer-modified photos 13 is the desired face and the desired selected set of modifications 12 to be used.

In a ninth step of the method the live video conference is processed and person 2 uses camera 15 to generate a video 17 that shows her face during the video conference 4 as shown in FIG. 2. Visual data modification means 9 receive the live video 17 and identify an area 16 in the video 17 that shows the face of person 2. Based on the desired selected data set of modifications 12 deep learning based application 7 uses visual data modification means 9 to continuously generate the computer-modified visual of the desired selected face of person 2. This means that even during all the movements of the face of person 2 and all facial expressions person 2 does during the video conference 4, her visual is continuously computer-modified to make her look more competent. This means that continuously her chin is modified to appear less wide and the cheeks less full and her eyebrows are lowered as shown in FIG. 6. Visual data modification means 9 then replace the identified area 16 in the video 17 from the camera 15 with the computer-modified visual of person 2 and send this modified video with the computer-modified visual of person 2 as video stream for the video conference 4. As a result, person 2 in video conference 4 appears with a visual that provides a first impression to the other participants of the video conference 4 of a very competent person. This gives person 2 a strong advantage in negotiations during the video conference 4.

In a preferred embodiment modification data base 11 may store data about objects a person may wear like glasses or earrings to change his/her first impression. In an even preferred embodiment person 2 upfront uploads visuals of his/her personal objects, so for instance a photo of her five different glasses and her ten different earrings. Deep learning based application 7 based on these data stored in modification data base 11 may generate further sets of modifications 12 where for instance glasses are overlaid over the visual of person 2 as shown in FIG. 2. This further extends the possibilities to improve the desired characteristic in the computer-modified visual of person 2.

In another embodiment person 2 may select to be shown only computer-modified visuals of her face in method step seven that are based on the table in FIG. 5. So these computer-modifications in principle all would be possible with invasive and/or minimally invasive cosmetic and medical treatments on a real person and therefore the computer-visuals shown on display 14 may look more realistic than others.

In a further embodiment, a dating App may use the method of the invention. In the profile of the dating App a man/woman may select a live chat with a person he/she would like to meet. To improve his/her chance in this live chat the person may choose to improve his characteristic "trustworthy" or "dominant" and select the extent of improvement by selecting his/her computer-modified visual. This enables a complete new and inventive way to connect potential future partners.

In another preferred embodiment of the invention steps 2 to 8 of the method claimed in claim 1 are processed for two or more characteristics or combinations of characteristics and sets of modifications selected for these different characteristics by the person are stored in the visual data modification means 9. The artificial intelligence is built to analyse the actual facial expressions of the face of the person in the video and to recognize content and/or tone of the person. The artificial intelligence for instance recognizes when person 2 gets angry or happy during the video conference. This recognition is based on visual and acoustical information provided in the video. A speech-to-text recognizer could in addition be used to enable a content analysis of the spoken words. So if person 2 talks about her mother being in hospital all these indications can be used to select one of the stored sets of modifications that fits this message, while another set of modification is selected a few seconds later, when person starts to negotiate the price of a product in the video conference.

This means that the appropriate stored set of modifications that supports the content and/or tone of the person is dynamically selected by the artificial intelligence and used by visual data modification means to dynamically modify the visual of the face of the person in the video with the selected set of modifications.

The term video has to be interpreted in its broadest sense and covers any sequence of visual data frames, which may display objects like real persons or animated characters. As animated character an avatar for a person could for instance be displayed, which could be an animal, phantasy creature or animated human being. The term video furthermore covers any two and three-dimensional visual representation of a live or stored data content. Video conferences like webinars, live presentations or distance teaching are covered as well.

The invention claimed is:

1. A method for providing a video with a computer-modified visual of a desired face of a person, comprising the steps of:
   A. generating a data set of visuals of faces and extracted face property data thereof linked to face characteristics data provided by a representative set of humans that rate the visuals of the faces about face characteristics of the visuals of faces and storing the data set in a database;
   B. extracting further face property data of the visuals of faces and use the extracted face property data together with the generated data set for training of an artificial intelligence to enable the artificial intelligence to provide an automated rating of the characteristics of the visuals of faces;
   C. providing at least one visual of the face of the person;
   D. inputting at least one characteristic of the face of the person to be improved;
   E. using the artificial intelligence to analyse the visual of the face of the person and to generate at least two data sets of modifications to improve a visual appearance of the person in at least two different ways towards the selected characteristic;
   F. modifying the visual of the face of the person based on the at least two data sets of modifications and generate two computer-modified visuals of the face of the person;
   G. displaying both computer-modified visuals of the face of the person;
   H. selecting one of the two computer-modified visuals as a desired face of the person; and
   I. providing a video that shows the face of the person and use a selected data set of modifications of the selected desired face of the person to modify the video to provide the video with the computer-modified visual of the desired face of the person.

2. The method according to claim 1, wherein the method comprises the following steps for method step I:
   continuously:
   identifying the visual of the face of the person in the video;
   modifying the visual of the identified face of the person based on the selected data set of modifications and generating the computer-modified visual of the desired face of the person;
   replacing the identified visual of the face of the person with the computer-modified visual of the desired face of the person in the video; and
   displaying the video with the replaced computer-modified visual of the desired face of the person.

3. The method according to claim 1, wherein steps A and B are processed to prepare a computer to process step E and wherein steps C to H are processed to select a desired face of the person and to process step I for the modification of a live video of a video conference.

4. The method according to claim 1, wherein method step E generates data sets of modifications to change the visual appearance of the person within the borders of visual modifications of a face achievable by a cosmetic and/or a medical treatment and/or manual changes of the visual appearance of the person.

5. The method according to claim 4, wherein method step B furthermore comprises the following step:
generating a data set of modifications of a face achievable by a cosmetic and/or a medical treatment and/or manual changes of the visual appearance of the person and store the data set in the database.

6. The method according to claim 5, wherein the method comprises the following further step of:
using predefined samples of tools to generate the data set of modifications of a face achievable by manual changes of the visual appearance of the person.

7. The method according to claim 5, wherein the method comprises the following further step of:
providing at least one visual of a personal object of the person to generate the data set of modifications of a face achievable by manual changes of the visual appearance of the person.

8. The method according to claim 1, wherein method steps C to H are processed for two or more characteristics or combinations of characteristics and data sets of modifications selected for the different characteristics are stored and that the artificial intelligence is built to analyse the actual facial expressions of the face of the person in the video and to recognize content and/or tone of the person and to select the appropriate stored data set of modifications that supports the content and/or tone of the person and to dynamically modify the visual of the face of the person in the video with the selected data set of modifications.

9. The method according to claim 1, wherein the method comprises the following further step of:
pre-processing the provided visual of the face of the person to standardize the provided visual of the face of the person prior to the analysis of the artificial intelligence processing, wherein pre-processing includes one or more of the following steps:
cut-out the background behind the face from the visual;
cut-out the ears of the face of the person to reduce a visual influence of the person;
cut-out an item of clothes; and
cut-out hair of the person.

10. A device for providing a video with a computer-modified visual of a desired face of a person, the device comprising:
a computer-readable medium having stored thereon a deep learning based application having instructions which, when executed by the device, cause the device to operate to:
generate a data set of visuals of faces and extracted face property data thereof linked to face characteristics data provided by a representative set of humans that rate the visuals of the faces about the face characteristics of the visuals of faces and store the data set in a database;
extract further face property data of the visuals of faces and use the extracted face property data together with the generated data set for training of an artificial intelligence to enable the artificial intelligence to provide an automated rating of the characteristics of the visuals of faces;
use the artificial intelligence to analyse a visual of a face of a person and to generate at least two data sets of modifications to improve the visual appearance of the person in at least two different ways towards a selected characteristic;
modify the visual of the face of the person based on both data sets of modifications and generate two computer-modified visuals of the face of the person; and
modify a video that shows the face of the person by the use of a selected data set of modifications of a selected desired face of the person to modify the video to provide a video with a computer-modified visual of the selected desired face of the person.

11. A non-transitory computer readable medium storing a computer-program comprising instructions which, when the program is executed by a device, causes the device to carry out the steps of:
A. generating a data set of visuals of faces and extracted face property data thereof linked to face characteristics data provided by a representative set of humans that rate the visuals of the faces about face characteristics of the visuals of faces and storing the data set in a database;
B. extracting further face property data of the visuals of faces and use the extracted face property data together with the generated data set for training of an artificial intelligence to enable the artificial intelligence to provide an automated rating of the characteristics of the visuals of faces;
C. providing at least one visual of the face of the person;
D. inputting at least one characteristic of the face of the person to be improved;
E. using the artificial intelligence to analyse the visual of the face of the person and to generate at least two data sets of modifications to improve a visual appearance of the person in at least two different ways towards the selected characteristic;
F. modifying the visual of the face of the person based on the at least two data sets of modifications and generate two computer-modified visuals of the face of the person;
G. displaying both computer-modified visuals of the face of the person;
H. selecting one of the two computer-modified visuals as a desired face of the person; and
I. providing a video that shows the face of the person and use a selected data set of modifications of the selected desired face of the person to modify the video to provide the video with the computer-modified visual of the desired face of the person.

12. The method according to claim 6, wherein the predefined samples of tools include at least (i) a particular pair of glasses, (ii) at least one earring, or (iii) a combination of (i) and (ii).

* * * * *